(12) United States Patent
Witzig et al.

(10) Patent No.: US 8,507,518 B2
(45) Date of Patent: Aug. 13, 2013

(54) METHOD OF TREATING MANTLE CELL LYMPHOMA

(75) Inventors: Thomas E. Witzig, Rochester, MN (US); Scott H. Kaufmann, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 13/078,272

(22) Filed: Apr. 1, 2011

(65) Prior Publication Data

US 2011/0184010 A1    Jul. 28, 2011

Related U.S. Application Data

(63) Continuation of application No. 10/979,284, filed on Nov. 2, 2004, now abandoned.

(60) Provisional application No. 60/517,329, filed on Nov. 4, 2003.

(51) Int. Cl.
*A61K 31/44* (2006.01)

(52) U.S. Cl.
USPC ........................................... 514/291

(58) Field of Classification Search
None
See application file for complete search history.

(56) References Cited

U.S. PATENT DOCUMENTS

| | | | |
|---|---|---|---|
| 5,362,718 A | 11/1994 | Skotnicki et al. | |
| 6,277,983 B1 | 8/2001 | Shaw et al. | |
| 6,432,973 B1 | 8/2002 | Zhu et al. | |
| 7,189,735 B2 | 3/2007 | Dukart et al. | |
| 7,781,446 B2 | 8/2010 | Dukart et al. | |
| 8,026,276 B2 | 9/2011 | Rubino et al. | |
| 2002/0091137 A1 | 7/2002 | Dukart et al. | |
| 2002/0183239 A1 | 12/2002 | Gibbons, Jr. et al. | |
| 2002/0198137 A1 | 12/2002 | Dukart et al. | |
| 2003/0008923 A1 | 1/2003 | Dukart et al. | |
| 2003/0050222 A1* | 3/2003 | Rabindran et al. | 514/1 |
| 2004/0167152 A1* | 8/2004 | Rubino et al. | 514/291 |
| 2004/0258662 A1 | 12/2004 | Gibbons et al. | |
| 2005/0272758 A1 | 12/2005 | Bayever | |
| 2007/0142425 A1 | 6/2007 | Dukart et al. | |
| 2011/0294845 A1 | 12/2011 | Rubino et al. | |

FOREIGN PATENT DOCUMENTS

| | | |
|---|---|---|
| WO | WO95/28406 | 10/1995 |
| WO | WO01/23395 A3 | 4/2001 |
| WO | WO02/24706 A2 | 3/2002 |
| WO | WO02/40000 | 5/2002 |
| WO | WO02/098416 | 12/2002 |
| WO | WO03/020266 A1 | 3/2003 |
| WO | WO03/064383 | 8/2003 |
| WO | WO2005/047252 A1 | 5/2005 |

OTHER PUBLICATIONS

Engel et al. Cancer Invest., 2007, vol. 25, No. 8, pp. 733-737 (Abstract attached).*
Atkins et al. J. Clin. Oncol., Mar. 1, 2004, vol. 22, No. 5, pp. 909-918.*
International Search Report and Written Opinion dated Mar. 9, 2005 issued in corresponding International Patent Application No. PCT/US2004/035900.
Office Action dated Jul. 15, 2009 issued in corresponding Australian patent application No. 2004289213.
Office Action dated Mar. 7, 2008 issued in corresponding Chinese patent application No. 200480039722.2.
Opposition dated Mar. 24, 2006 filed by the Asociacion Industrial de Laboratorios Farmaceuticos AG in Chilean patent application No. 2852-2004.
Agent's letter dated Nov. 25, 2008 providing summary of Examiner's comments from an Office Action issued in Chilean patent application No. 2852-2004 (confidential information redacted).
Observations dated Aug. 26, 2005 filed by Enrique Aguilar Sandoval in Guatemalan patent application No. PI-20040224.
Communication dated Oct. 9, 2006 issued in European patent application No. 04796697.3.
Opposition dated Jun. 2, 2006 presented by ALAFAR in Ecuadorean patent application No. SP-04-5294.
Office Action dated Apr. 2, 2009 issued in Israeli patent application No. 175128.
Office Action dated Sep. 9, 2010 issued in Indian patent application No. 1480/KOLNP/2006.
Office Action dated Oct. 27, 2009 issued in Indian patent application No. 1480/KOLNP/2006.
Office Action issued on Jul. 28, 2008 in Russian patent application No. 2006119451.
Agent's letter dated Jul. 13, 2007 providing translation of Examiner's comments from an Office Action issued in Peruvian patent application No. 1059-2004/OIN.
Agent's letter dated Feb. 7, 2008 providing summary of Examiner's comments from an Office Action issued in Peruvian patent application No. 1059-2004/OIN.
Examination report dated Sep. 18, 2008 issued in New Zealand patent application No. 546881.
Office action dated Nov. 2, 2007 issued in Malaysian patent application No. PI 20044512.
Agent's letter dated Nov. 18, 2010 providing translation of Examiner's comments from an Office Action issued in Japanese patent application No. P207864 (confidential information redacted).
Alberts and Dorr, New Perspectives on an Old Friend: Optimizing Carboplatin for the Treatment of Solid Tumors, Oncologist, 3(1):15-34 (1998).
Alexandre et al, La rapamycine et le CCI-779 (Rapamycin and CCI-779), Cancer Bulletin, 86(10):808-811 (Oct. 1999).

(Continued)

*Primary Examiner* — James D Anderson
(74) *Attorney, Agent, or Firm* — Howson & Howson LLP; Cathy A. Kodroff; David Rubin

(57) ABSTRACT

This invention provides the use of rapamycin 42-ester with 3-hydroxy-2-(hydroxymethyl)-2-methylpropionic acid (CCI-779) in the treatment or inhibition of mantle cell lymphoma.

13 Claims, No Drawings

(56) References Cited

OTHER PUBLICATIONS

Ansell et al, Low-Dose, Single-Agent Temsirolimus for Relapsed Mantle Cell Lymphoma: A Phase 2 Trial on the North Central Cancer Treatment Group, Cancer, 113:508-14 (Aug. 1, 2008).
Callea et al, Retrospective Analysis of Mantel cell Lymphoma: Experience of the "Gruppo Italiano Per Lo Studio Dei Linfomi" (GISL), Haematologica, 83(11):993-7 (Nov. 1998).
CCI-779 shows positive safety profile and potential anti-tumor activity, Oct. 13, 2000, http://www.eurekalert.org/pub_releases/2000-10/K-Csps-1210100.php.
Clackson et al, Broad Anti-tumor Activity of ap23573, an mTOR Inhibitor in Clinical Development, Proceedings of the American Society of Clinical Oncology 22:220, (2003) (Abstract 882).
Coiffier et al, Rituximab (anti-CD20 monoclonal antibody) for the treatment of patients with relapsing or refractory aggressive lymphoma: a multicenter phase II study, Blood, 92(6):1927-32 (Sep. 1998).
Costa, Aspects of mTOR Biology and the Use of mTOR Inhibitors in Non-Hodgkin's Lymphoma, Cancer Treatment Reviews, 33(1), pp. 78-84, (Feb. 2007).
Decaudin et al, Is Mantle Cell Lymphoma a Sex-Related Disease?, Leukemia and Lymphoma, 37(1-2):181-4 (Mar. 2000).
Elit, CCI-779 Wyeth, Current Opinion in Investigational Drugs pp. 3(8):1249-1253 (Aug. 2002).
Fayad et al, Linfoma de células del manto: una revisión (Mantle Cell Lymphoma: A Review), Hematologia—Citacinas, Immunoterapia Y Terapia Celular, 6(2):100-112 (2003).
Hashimoto et al, Multiple Lymphomatous Polyposis of the Gastrointestinal Tract is Heterogenous Group that Includes Mantle Cell Lymphoma and Follicular Lymphoma: Analysis of Somatic Mutation of Immunoglobulin Heavy Chain Gene Variable Region, Hum Pathol, 30(5):581-7 (May 1999).
Hess et al, Phase III Study to Evaluate Temsirolimus Compared with Investigator's Choice Therapy for the Treatment of Relapsed or Refactory Mantle Cell Lymphoma, Journal of Clinical Oncology, 27(23):3822-9 (Jul. 6, 2009).
Hidalgo et al, The Rapamycin-Sensitive Signal Transduction Pathway as a Target for Cancer Therapy, Oncogene, 19(56):6680-6 (Dec. 2000).
Hidalgo, A Phase I and Pharmacological Study of CCI-779, a Rapamycin Ester Cell Cycle Inhibitor, Annals of Oncology, 11(Suppl. 4):133 (Oct. 2000).
Hiddemann et al, Mantle-Cell Lymphomas Have more Widespread Disease and a Slower Response to Chemotherapy compared with follicle-Center Lymphomas: results of a Prospective Comparative Analysis of the German Low-Grade Lymphoma Study Group, J Clinical Oncology, 16(5):1922-30 (May 1998).
Huang et al, Inhibitors of Mammalian Target of Rapamycin as Novel Antitumor Agents: From Bench to Clinic, Current Opinion in Investigational Drugs, 3(2):295-304 (Feb. 2002).
Johnson et al, Antagonistic Interplay Between Antimitotic and G1-S Arresting Agents Observed in Experimental Combination Therapy, Clinical Cancer Research, (9):2559-65, (Sep. 1999).
Molina et al, Mantle Cell Lymphoma, in Leukaemic Phase with Prominent Splenomegaly. A Report of Eight Cases With Similar Clinical Presentation and Aggressive Outcome Virchows Arch. 437(6):591-8 (Dec. 2000).
Oinonen et al, Mantle Cell Lymphoma: Clinical Features, Treatment and Prognos of 94 Patients, European Journal of Cancer, 34(3):329-36 (Feb. 1998).
Robins, P., Poster Highlights 1, iDrugs, 2(6):534-7 Paragraph entitled CCI-779, (1999).
Samaha et al, Mantle Cell Lymphoma: A Retrospective Study of 121 Cases, Leukemia, 12(8):1281-7 (Aug. 1998).
Weisenburger et al, Mantle Cell Lymphoma. A Clinicopathologic Study of 68 Cases from the Nebraska Lymphoma Study Group, American Journal of Hematology 64(3):190-6 (Jul. 2000).
Witzig et al, A Phase II Trial of the Rapamycin Analog CCI-779 in Previously Treated Mantle Cell Non-Hodgkin's Lymphoma: Interim Analysis of 18 Patients, Abstract # 2374, p. 643a, Blood (Nov. 16, 2003).
Witzig et al, Anti-Tumor Activity of Low-Dose Single Agent CCI-779 for Relapsed Mantel Cell Lymphoma: A Phase II Trial in the North Central Cancer Treatment Group, Journal of Clinical Oncology, 2005 ASCO Annual Meeting Proceedings, 23(16S):6504 Supplement Part I of II (Jun. 1, 2005).
Witzig et al, Inhibition of the Phosphatidylinositol 3-Kinase/Mammalian Target of Rapamycin Pathway in Hematologic Malignancies, Current Treatment Options in Oncology, 7:285-294 (Jul. 2006).
Witzig et al, Phase II Trial of Single-Agent Temsirolimus (CCI-779) for Relapsed Mantle Cell Lymphoma, Journal of Clinical Oncology, 23(23):5347-5356 (Aug. 10, 2005).
Wong et al, Mantle Cell Lymphoma in Leukemic Phase: Characterization of its Broad Cytologic Spectrum with Emphasis on the Importance of Distinction from Other Chronic Lymphoproliferative Disorders, Cancer 86(5):850-7 (Sep. 1, 1999).
Office Action dated Dec. 6, 2006 issued in U.S. Appl. No. 10/979,284.
Amendment dated Feb. 28, 2007 filed in U.S. Appl. No. 10/979,284.
Office Action dated May 8, 2007 issued in U.S. Appl. No. 10/979,284.
Amendment dated Jul. 6, 2007 filed in U.S. Appl. No. 10/979,284.
Advisory Action dated Aug. 21, 2008 issued in U.S. Appl. No. 10/979,284.
Office Action dated Feb. 8, 2008 issued in U.S. Appl. No. 10/979,284.
Amendment dated May 6, 2008 filed in U.S. Appl. No. 10/979,284.
Office Action dated Jul. 25, 2008 issued in U.S. Appl. No. 10/979,284.
Amendment dated Oct. 24, 2008 filed in U.S. Appl. No. 10/979,284.
Office Action dated Nov. 17, 2008 issued in U.S. Appl. 10/979,284.
Amendment dated Feb. 17, 2009 filed in U.S. Appl. 10/979,284.
Office Action dated May 5, 2009 issued in U.S. Appl. 10/979,284.
Amendment dated Aug. 5, 2009 filed in U.S. Appl. 10/979,284.
Office Action dated Aug. 31, 2009 issued in U.S. Appl. 10/979,284.
Appeal Brief dated Apr. 23, 2010 filed in U.S. Appl. No. 10/979,284.
Examiner's Answer dated Jul. 8, 2010 issued in U.S. Appl. 10/979,284.
Reply Brief dated Sep. 7, 2010 filed in U.S. Appl. 10/979,284.
Appeal decision dated Feb. 1, 2011 issued in U.S. Appl. No. 10/979,284.
Witzens-Harig M, et al. Current treatment of mantle cell lymphoma: results of a national survey and consensus meeting, Springer, Aug. 2012.

* cited by examiner

METHOD OF TREATING MANTLE CELL LYMPHOMA

CROSS-REFERENCE TO RELATED APPLICATIONS

This application in a continuation of U.S. patent application Ser. No. 10/979,284, filed Nov. 2, 2004, now abandoned, which claims the benefit under 35 USC 119(e) of prior U.S. Provisional Patent Application No. 60/517,329, filed Nov. 4, 2003, now expired. The applications are incorporated by reference in their entirely.

STATEMENT REGARDING FEDERALLY SPONSORED RESEARCH OR DEVELOPMENT

This invention was made with government support under Grant No. CA 25224 awarded by the National Institutes of health. The United States government has certain rights in this invention.

BACKGROUND OF THE INVENTION

This invention relates to the use of rapamycin 42-ester with 3-hydroxy-2-(hydroxymethyl)-2-methylpropionic acid (CCI-779) in the treatment or inhibition of mantle cell lymphoma.

Rapamycin 42-ester with 3-hydroxy-2-(hydroxymethyl)-2-methylpropionic acid (CCI-779) is an ester of rapamycin. Rapamycin, also termed sirolimus, is a macrocyclic triene antibiotic produced by *Streptomyces hygroscopicus*. The preparation and use of hydroxyesters of rapamycin, including CCI-779, are described in U.S. Pat. Nos. 5,362,718 and 6,277,983.

CCI-779 has been described as having in vitro and in vivo activity against a number of tumor cell types. It is hypothesized that CCI-779 delays the time to progression of tumors or time to tumor recurrence. This mechanism of action is more typical of cytostatic rather than cytotoxic agents and is similar to that of sirolimus.

CCI-779 binds to and forms a complex with the cytoplasmic protein FKBP, which inhibits an enzyme, mTOR (mammalian target of rapamycin, also known as FKBP12-rapamycin associated protein [FRAP]). Inhibition of mTOR's kinase activity inhibits a variety of signal transduction pathways, including cytokine-stimulated cell proliferation, translation of mRNAs for several key proteins that regulate the G1 phase of the cell cycle, and IL-2-induced transcription, leading to inhibition of progression of the cell cycle from G1 to S.

Mantle cell lymphoma, a cancer of the B-lymphocytes housed in the mantle regions of the lymph nodes, is a unique subtype of non-Hodgkin's lymphoma (NHL) which is characterized by a specific chromosomal translocation of the bcl-1 gene (t(11;14)(q13:q32)) and subsequent over-production of the gene product cyclin D1. The proto-oncogene bcl-1 (which stands for B-cell lymphoma/leukemia) is one of five genes on the section of chromosome 11 which are translocated in MCL, but it is the only one expressed in MCL. The unique nature of lymphocytes and, in particular, the site bcl-1 occupies on chromosome 14 account for at least some of the bizarre behavior of MCL cells.

MCL represents approximately 10% of all NHL. The median age of onset is approximately 60 years and there is a higher incidence in males [Decaudin, D., et al., Leuk Lymphoma 37: 181-4 (2000)]. Patients typically present in advanced stage and extranodal sites are often involved. For example, some patients present with prominent lymphocytosis and may be mistaken for chronic lymphocytic leukemia [Wong, K. F., et al., Cancer 86: 850-7 (1999)]. Others present with multiple polyps in the colon that can produce gastrointestinal bleeding [Hashimoto, Y., et al., Hum Pathol 30: 581-7 (1999)]. Another unusual presentation is that of massive splenomegaly and minimal lymphadenopathy [Molina, T. J., et al., Virchows Arch 437: 591-8 (2000)]. Patients with MCL have been demonstrated to have a significantly worse prognosis than those with other low-grade histologies with a median survival of 3-4 years [Weisenburger, D. D., et al., Am J Hematol 64: 190-6 (2000); Hiddemann, W., et al., Journal of Clinical Oncology 16: 1922-30 (1998); Samaha, H., et al., Leukemia 12: 1281-7, (1998); Callea, V., et al., Haematologica 83: 993-7 (1998)].

The treatment of MCL has remained problematic despite the availability of purine nucleoside analogues, stem cell transplantation, and monoclonal antibody therapy with rituximab. Each of these modalities can produce tumor responses in MCL but the disease typically recurs and requires additional therapy. There is no one treatment regimen that can be considered the treatment of choice for patients with new, untreated MCL. Most patients are treated with combinations of rituximab and chemotherapy—usually R-CHOP or a purine nucleoside analogue and rituximab. Patients who are eligible for high-dose therapy with stem cell support are usually transplanted in first remission.

Less than 50% of MCL patients achieve a complete remission (CR) with current therapy and few patients achieve durable remissions. The typical scenario is that the patient will respond to chemotherapy, but the responses are usually partial and the time to progression short [Oinonen, R., et al., European Journal of Cancer 34: 329-36 (1998)].

Mantle cell lymphoma remains a difficult disease to treat once it has relapsed and patients are typically treated with multiple regimens with a short time to progression between treatments.

SUMMARY OF THE INVENTION

The invention provides for the use of a CCI-779 in preparing a medicament for treating or inhibiting mantle cell lymphoma in a subject.

In one aspect, the invention provides a pharmaceutical composition for treating or inhibiting mantle cell lymphoma which comprises a CCI-779 in unit dosage form in association with a pharmaceutically acceptable carrier.

In another aspect, the invention provides a pharmaceutical pack containing a course of treatment of mantle cell lymphoma for one individual mammal, comprising a container having a CCI-779 in unit dosage form.

Other aspects and advantages of the invention will be apparent from the following detailed description of the invention.

DETAILED DESCRIPTION OF THE INVENTION

Thus, the invention provides a method and kits useful in treatment or inhibition of mantle cell lymphoma.

As used in accordance with this invention, the term "treatment" means treating a mammal having mantle cell lymphoma by providing said mammal with an effective amount of a CCI-779 with the purpose of inhibiting growth of the lymphoma in such mammal, eradication of the lymphoma, or palliation of the lymphoma.

As used in accordance with this invention, the term "inhibition" means inhibiting the onset or progression of mantle cell lymphoma in a mammal having or susceptible to developing such disease by providing said mammal an effective amount of CCI-779.

As used in accordance with this invention, the term "providing," means either directly administering CCI-779 or administering a prodrug, derivative, pharmaceutical salt, or analog of CCI-779 which will form an effective amount of CCI-779 in the body. Throughout this specification and claims, the term "a CCI-779" encompasses CCI-779, and such prodrugs, derivatives, pharmaceutical salts, or analogs thereof, which provide an effective amount of CCI-779 to the subject.

The preparation of CCI-779 is described in U.S. Pat. No. 5,362,718, which is hereby incorporated by reference. A regiospecific synthesis of CCI-779 is described in U.S. Pat. No. 6,277,983, which is hereby incorporated by reference. Still another regiospecific method for synthesis of CCI-779 is described in U.S. patent application Ser. No. 10/903,062, filed Jul. 30, 3004, and its counterpart, International Patent Application PCT/US2004/22860, filed Jul. 15, 2004.

Although the invention illustrates the use of CCI-779, it is anticipated that other rapamycins can be utilized in the invention in the place of CCI-779. The term "a rapamycin" defines a class of immunosuppressive compounds which contain the basic rapamycin nucleus. The rapamycins of this invention include compounds which may be chemically or biologically modified as derivatives of the rapamycin nucleus, while still retaining immunosuppressive properties. Accordingly, the term "a rapamycin" includes esters, ethers, oximes, hydrazones, and hydroxylamines of rapamycin, as well as rapamycins in which functional groups on the rapamycin nucleus have been modified, for example through reduction or oxidation. The term "a rapamycin" also includes pharmaceutically acceptable salts of rapamycins, which are capable of forming such salts, either by virtue of containing an acidic or basic moiety.

It is preferred that the rapamycin compound is selected from among rapamycin, [Rapamune™ brand sirolimus, Wyeth, Madison, N.J.], or 42-O-(2-hydroxy)ethyl rapamycin. Other suitable rapamycins include, e.g., AP23573 [Ariad], FK-506, RAD001 (everolimus) and TAFA-93, a prodrug of rapamycin [Isotechnika Inc].

The ability of a CCI-779 to treat or inhibit mantle cell lymphoma was evaluated in a clinical trial. Briefly, 18 patients (mean age 72 years, range 38-89 years) were treated with an intravenous dose of 250 mg CCI-779 on days 1, 8, 15, and 22 of a 4 week treatment cycle, for up to a maximum of 12 cycles. Of these patients, 15 were stage IV, 2 were stage III, and 1 was stage II. The overall response rate was 44.4% (95% CI; 24%-68%) and thus satisfied the criteria as early evidence of efficacy in this patient group. One patient had a complete response (CR), and 7 patients had a partial response (PR). Only 3 patients progressed before the end of the cycle. Based on the results obtained in this clinical trial, CCI-779 is useful in the treatment or inhibition of mantle cell lymphoma.

When a CCI-779 is used in the treatment or inhibition of mantle cell lymphoma, it is projected that a subject will be provided with a weekly dosage of 10 to 250 mg of CCI-779 per week. Treatment typically consists of a monthly cycle composed of weekly dosage administrations, although weekly or bi-weekly cycles may be selected. A subject may undergo from one to twelve continuous monthly cycles. Alternatively, a subject may undergo one cycle, cease treatment, and then undergo another cycle.

Oral or intravenous infusion are the preferred routes of administration, with intravenous being more preferred. Initial intravenous dosages are typically projected to be tenfold less than the oral dosages. For example, intraveous dosages may be in the range of 10 mg/week to 175 mg/week, or from 20 mg/week to 150 mg/week, or more desirably, from 25 mg/week to 75 mg/week; whereas, oral doses may be in the range of 100 mg/week to 250 mg/week, 125 mg/week to 225 mg/week, or 150 mg/week to 200 mg/week. Precise dosages for oral, parenteral, nasal, or intrabronchial administration will be determined by the administering physician based on experience with the individual subject treated.

Treatment will generally be initiated with small dosages less than the optimum dose of the compound. Thereafter the dosage is increased until the optimum effect under the circumstances is reached. Optionally, the dosage is then decreased for a week, biweek, or cycle, as desired or necessary.

Preferably, the pharmaceutical composition is in unit dosage form, e.g. as tablets, capsules, or prefilled vials or syringes. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed. Preferred oral formulations for rapamycin 42-ester with 3-hydroxy-2-(hydroxymethyl)-2-methylpropionic acid are disclosed in US Published Patent Application, US 2004-0077677 A1 (also U.S. Ser. No. 10/663,506), which is hereby incorporated by reference.

In some cases it may be desirable to administer the compounds directly to the airways in the form of an aerosol.

The compounds may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils. Preferred injectable formulations for rapamycin 42-ester with 3-hydroxy-2-(hydroxymethyl)-2-methylpropionic acid are disclosed in US 2004-0167152 (also U.S. Ser. No. 10/626,943), which is hereby incorporated by reference.

In this embodiment, the injectable formulation useful in the invention provides a CCI-779 cosolvent concentrate containing an parenterally acceptable solvent and an antioxidant as described above and a parenteral formulation containing a CCI-779, composed of a CCI-779, an parenterally acceptable cosolvent, an antioxidant, a diluent solvent, and a surfactant. Any given formulation useful in this invention may contain multiple ingredients of each class of component. For example, a parenterally acceptable solvent can include a non-alcoholic solvent, an alcoholic solvent, or mixtures thereof. Examples of suitable non-alcoholic solvents include, e.g., dimethylacetamide, dimethylsulfoxide or acetonitrile, or mixtures thereof. "An alcoholic solvent," may contain one or more alcohols as the alcoholic solvent component of the formulation. Examples of solvents useful in the formulations invention include, without limitation, ethanol, propylene glycol, polyethylene glycol 300, polyethylene glycol 400, polyethylene glycol 600, polyethylene glycol 1000, or mixtures thereof. These cosolvents are particularly desirable because degradation via oxidation and lactone cleavage occurs to a lower extent for these cosolvents. Further, ethanol and propylene glycol can be combined to produce a less flammable product, but larger amounts of ethanol in the mixture generally result in better chemical stability. A concentration of 30 to 100% v/v of ethanol in the mixture is preferred.

In this embodiment, the stability of a CCI-779 in parenterally acceptable alcoholic cosolvents is enhanced by addition of an antioxidant to the formulation. Acceptable antioxidants include, but are not limited to, citric acid, d,l-α-tocopherol, BHA, BHT, monothioglycerol, ascorbic acid, propyl gallate, and mixtures thereof. Generally, the parenteral formulations useful in this embodiment of the invention will contain an antioxidant component(s) in a concentration ranging from 0.001% to 1% w/v, or 0.01% to 0.5% w/v, of the cosolvent concentrate, although lower or higher concentrations may be desired. Of the antioxidants, d,l-α-tocopherol is particularly desirable and is used at a concentration of 0.01 to 0.1% w/v with a preferred concentration of 0.075% w/v of the cosolvent concentrate.

In certain embodiments, the antioxidant component of the formulation of the invention also exhibits chelating activity. Examples of such chelating agents include, e.g., citric acid, acetic acid, and ascorbic acid (which may function as both a classic antioxidant and a chelating agent in the present formulations). Other chelating agents include such materials as are capable of binding metal ions in solution, such as ethylene diamine tetra acetic acid (EDTA), its salts, or amino acids such as glycine are capable of enhancing the stability of a CCI-779. In some embodiments, components with chelating activity are included in the formulations of the invention as the sole "antioxidant component". Typically, such metal-binding components, when acting as chelating agents are used in the lower end of the range of concentrations for the antioxidant component provided herein. In one example, citric acid enhanced the stability of a CCI-779 when used at a concentration of less than 0.01% w/v. Higher concentrations are less stable solutions and thus, less desirable for products to be subject to long-term storage in liquid form. Additionally, such chelating agents may be used in combination with other antioxidants as part of the antioxidant component of the invention. For example, an acceptable formulation may contain both citric acid and d,l-α-tocopherol. Optimal concentrations for the selected antioxidant(s) can be readily determined by one of skill in the art, based upon the information provided herein.

Advantageously, in certain embodiments of the parenteral formulations useful in the invention, precipitation of a CCI-779 upon dilution with aqueous infusion solutions or blood is prevented through the use of a surfactant contained in the diluent solution. The most important component of the diluent is a parenterally acceptable surfactant. One particularly desirable surfactant is polysorbate 20 or polysorbate 80. However, one of skill in the art may readily select other suitable surfactants from among salts of bile acids (taurocholate, glycocholate, cholate, deoxycholate, etc.) which are optionally combined with lecithin. Alternatively, ethoxylated vegetable oils, such as a pegylated castor oil [e.g., such as PEG-35 castor oil which is sold, e.g., under the name Cremophor EL, BASF], vitamin E tocopherol propylene glycol succinate (Vitamin E TGPS), and polyoxyethylene-polyoxypropylene block copolymers can be used in the diluent as a surfactant, as well as other members of the polysorbate family such as polysorbate 20 or 60 Other components of the diluent may include water, ethanol, polyethylene glycol 300, polyethylene 400, polyethylene 600, polyethylene 1000, or blends containing one or more of these polyethylene glycols, propylene glycol and other parenterally acceptable cosolvents or agents to adjust solution osmolarity such as sodium chloride, lactose, mannitol or other parenterally acceptable sugars, polyols and electrolytes. It is expected that the surfactant will comprise 2 to 100% w/v of the diluent solution, 5 to 80% w/v, 10 to 75% w/v, 15 to 60% w/v, and preferably, at least 5% w/v, or at least 10% w/v, of the diluent solution.

A parenteral formulation useful in the invention can be prepared as a single solution, or preferably can be prepared as a cosolvent concentrate containing a CCI-779, an alcoholic solvent, and an antioxidant, which is subsequently combined with a diluent that contains a diluent solvent and suitable surfactant. Prior to use, the cosolvent concentrate is mixed with a diluent comprising a diluent solvent, and a surfactant. When CCI-779 is prepared as a cosolvent concentrate according to this invention, the concentrate can contain concentrations of a CCI-779 from 0.05 mg/mL, from 2.5 mg/mL, from 5 mg/mL, from 10 mg/mL or from 25 mg/mL up to approximately 50 mg/ml. The concentrate can be mixed with the diluent up to approximately 1 part concentrate to 1 part diluent, to give parenteral formulations having concentrations of a CCI-779 from 1 mg/mL, from 5 mg/mL, from 10 mg/mL, from 20 mg/mL, up to approximately 25 mg/ml. For example the concentration of a CCI-779 in the parenteral formulation may be from about 2.5 to 10 mg/mL. This invention also covers the use of formulations having lesser concentrations of a CCI-779 in the cosolvent concentrate, and formulations in which one part of the concentrate is mixed with greater than 1 part of the diluent, e.g., concentrate:diluent in a ratio of about 1:1.5, 1:2, 1:3, 1:4, 1:5, or 1:9 v/v and so on, to a CCI-779 parenteral formulations having a CCI-779 concentration down to the lowest levels of detection.

Typically the antioxidant may comprise from about 0.0005 to 0.5% w/v of the formulation. The surfactant may for example comprise from about 0.5% to about 10% w/v of the formulation. The alcoholic solvent may for example comprise from about 10% to about 90% w/v of the formulation.

The parenteral formulations useful in this invention can be used to produce a dosage form that is suitable for administration by either direct injection or by addition to sterile infusion fluids for intravenous infusion.

For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The components of the invention may be in the form of a kit of parts. The invention therefore includes a product containing a CCI-779 for use in treatment or inhibition of mantle cell lymphoma in a mammalian subject in need thereof. The invention also includes a pharmaceutical pack containing a course of treatment of mantle cell lymphoma for one individual mammalian subject, wherein the pack contains units of a CCI-779 or 42-O-(2-hydroxy)ethyl rapamycin in unit dosage form. In one embodiment, the product contains a CCI-779 in a form ready for administration. Alternatively, the product can contain a CCI-779 as a concentrate which can be mixed with a suitable diluent that is optionally provided in the product. In yet another embodiment, the product contains a CCI-779 in solid form and, optionally, a separate container with a suitable solvent or carrier for the CCI-779. Still other components on the kit, e.g., instructions for dilution, mixing and/or administration of the product, other contains, syringes, needles, etc., will be readily apparent to one of skill in the art.

The following examples are illustrative of the present invention, but are not a limitation thereof.

Example 1

Anti-Tumor Activity of Single-Agent CCI-779 for Relapsed Mantle Cell Lymphoma: a Phase II Trial in the North Central Cancer Treatment Group Mantle cell lymphoma (MCL) is characterized by a t(11; 14) resulting in overexpression of cyclin D1, a member of the phosphatidylinositol 3 kinase (PI3K) pathway. This study tested whether CCI-779, which inhibits the PI3K pathway at the level of the mammalian target of rapamycin (mTOR) could produce tumor responses in patients with MCL.

A. Patients and Methods

This study was conducted through the North Central Cancer Treatment Group (NCCTG) cooperative group. Patients were eligible for this trial if they had previously received therapy and had relapsed. There was no limit on the number of prior therapies. All histologies were confirmed to be mantle cell lymphoma by central pathology review. Cyclin-D1 positivity was required by immunohistochemistry or t(11;14) detected by FISH. Patients were required to have measurable disease with a lymph node or tumor mass≧2 cm or malignant lymphocytosis with an ALC≧5,000; a life expectancy of ≧3 months, ECOG performance status of 0, 1, or 2; absolute neutrophil count (ANC)≧1,000; platelets≧75,000; hemoglobin≧8 g/dL; serum creatinine≦2× the upper limit of normal (UNL); serum bilirubin≦1.5 UNL; serum cholesterol≦350 mg/dL; and triglycerides≦400 mg/dL. Patients could not have known central nervous system involvement or HIV infection.

Patients were treated with a flat dose of 250 mg of CCI-779 diluted in 250 mL of normal saline and delivered IV over 30 minutes. Patients were pretreated with diphenhydramine 25-50 mg IV. Treatment was weekly and a cycle was considered 4 weeks. A complete blood count was performed each week and a full dose delivered if the platelet count was ≧50, 000 and the ANC≧1000 and there was no grade 3 non-hematologic toxicity (using the NCI Common Toxicity Criteria version 2). Patients who did not meet the retreatment criteria had the dose held until recovery and then the dose modified to a flat dose of 175, 125, 75, or 50 mg. Patients were not to receive prophylactic white blood cell growth factors to maintain dosing but could receive them at time of neutropenia at physician discretion. Erythropoietin could be used.

Patients were restaged after 1, 3, and 6 cycles and the response assessed as per the international workshop criteria. [B. D. Cheson, et al., "Report of an International Workshop to Standardize Response Criteria for Non-Hodgkin's Lymphomas", *Journal of Clinical Oncology*, Vol 17, Issue 4 (April), 1999: 1244]. Patients who progressed anytime or those patients with stable disease after 6 cycles went off study. Patients who had a complete remission (CR) or partial remission (PR) at 6 months were to receive 2 cycles past CR or a total of 12 months if PR and then observed without further therapy.

A single stage phase II study with an interim analysis was conducted to assess the proportion of previously treated mantle cell lymphoma patients who achieved a PR or better after treatment with CCI-779. This trial was designed to test the null hypothesis that the true response rate was at most 0.05. The smallest response rate that would indicate that this regimen was worth further study in this patient population was 0.20. The design was generated based on the parameters and assumptions of a two-stage Simon MinMax™ design, but where accrual was not suspended for the interim analysis. This study design required a maximum of 32 evaluable patients, where the interim analysis was performed after 18 patients had been accrued and followed for at least 24 weeks. An additional 3 patients were accrued to this cohort (for a maximum of 35 patients overall) to account for the possibilities of ineligibility, withdrawal from study prior to drug administration, or major violations. However, only the first 32 evaluable patients were used to evaluate the decision criteria for this design. At least one response in the first 18 evaluable patients needed to be observed in the interim analysis to continue accrual. At the time of the final analyses, a total of four or more responses were required to indicate that this regimen warrants further evaluation in this patient population. The proportion of responses were calculated, and 90% exact binomial confidence interval (CI) for the true response rate was calculated (with all eligible patients accrued) assuming that the number of responses was binomially distributed.

Duration of response was defined as the time from the date of documented response to the date of progression. Patients who went off treatment due to other reasons (e.g., adverse reactions, refusal of further treatment) were censored at that time. Time to progression was defined as the time from registration to the date of progression. Patients who died without disease progression were censored at the date of their last evaluation. If a patient died without documentation of disease progression, the patient was considered to have had disease progression at the time of death unless there was sufficient documented evidence to conclude that progression did not occur prior to death. Time to discontinuation of active treatment was defined as the time from registration to the date the decision was made to take the patient off active treatment. Patients who were still receiving treatment at the time of these analyses were censored at the date of their last evaluation. Overall survival was defined as the time from registration to death resulting from any cause. The distributions of these time-to-event endpoints were each estimated using the Kaplan-Meier method [J M Bland and D G Altman, "Survival probabilities (the Kaplan-Meier method)", *BMJ*, 317(7172): 1572 (Dec. 5, 1998)].

B. Patient Characteristics

A total of 35 patients were enrolled on this trial. One patient was declared ineligible after pathology review indicated that although the histology was consistent with MCL the cyclin D1 stain was negative. The patients tended to be older adults with a median age of 70 years (range: 38-89). Most patients (91%) had stage IV disease and were heavily pretreated with a median number of 3 prior therapies (mean, 4; range, 1-11). The majority of patients had failed rituximab, an alkylator agent such as cyclophosphamide, and an anthracycline such as doxorubicin. Over half of the patients had received a purine nucleoside analogue.

C. Clinical Outcomes

The overall response rate (ORR) was 38% (13/34; 90% CI: 24%-54%) with 1 CR, and 12 PRs. The tumor responses occurred rapidly, where the median time to response was 1 month (range, 1-8). Eight responses occurred after the first cycle evaluation, 3 were documented after 3 cycles, and 1 each after 4 and 8 months evaluations. The median duration of response for the 13 responders was 5.7 months (95% CI: 4-13.2 months). At the time of these analyses, 3 patients remain on treatment.

The median follow-up on living patients was 11 months (range: 6.7-24.6 months). Overall, 29 patients have had disease progression and 22 patients have died. No patients have had documented death without disease progression. The median time to progression was 6.2 months (95% CI: 3.8-9.4 months). The median overall survival was 12 months (95% CI: 6.7 months to not yet reached).

D. Safety and Tolerability

All 35 patients were included in the analysis of safety and tolerability. During the 30 minute infusion, CCI-779 was well-tolerated and there were no significant toxicities that occurred. Thrombocytopenia was the cause of most dose reductions and was rapidly reversible with drug delays of typically only one week. Only three patients required platelet transfusions, and four patients required red blood cell transfusions. Thirteen patients experienced grade 3 infections without concomitant neutropenia; two patients had febrile neutropenia and three had infection (grade 3) with neutropenia. One patient developed a right lower motor neuron facial palsy (Bell's palsy) and mental status changes and underwent an MRI scan and cerebral spinal fluid analysis that did not reveal evidence of involvement with MCL. The conclusion was that this was idiopathic Bell's palsy and indeed it eventually resolved. A possible relationship to CCI-779 could not be established nor eliminated. The patient who experienced blurred vision was diagnosed with retinitis due to reactivation of cytomegalovirus (CMV) infection. The patient had a history of CMV retinitis prior to enrollment on this study but the infection was not evident at the time of study entry.

The most common adverse events of all grades were thrombocytopenia (100%), hyperglycemia (91%), anemia (66%), neutropenia (77%), increased triglycerides (77%), mucositis (71%), fatigue (66%), infection without concomitant neutropenia (63%), rash (51%), nausea (49%), weight loss (46%), AST elevations (43%), abnormal taste (43%), loss of appetite (40%), hypercholesterolemia (40%), and sensory neuropathy (37%). No grade 5 events (i.e. deaths on treatment) were reported.

In terms of tolerability of the treatment regimen, only 4 patients completed the study as designed (1 CR, 2 PRs, and 1 stable disease patient who completed all 12 cycles). Of the remaining 28 patients who discontinued treatment, 1 patient was treated with alternative therapy without progression, 7 went off treatment due to adverse reactions, 4 refused further treatment, 1 patient was removed due to other medical problems, and 15 progressed on therapy. Of note is that those patients who refused further treatment or who went off for other medical problems discontinued this treatment regimen largely due to low grade adverse events and a perceived decline in quality of life. The median time to discontinuation of treatment was 3.7 months (95% CI: 3-6.2 months).

Dose reductions were necessary in all but 4 patients. Nine patients were able to receive 250 mg weekly for a median of 2.5 cycles (range, 1-8); the others required dose reductions in the first cycle. Of the 6 patients who received more than one cycle, 2 eventually required a dose reduction. The median dose received per month on study was 175 mg in all patients; 125 mg in responding patients; and 175 mg in non-responders.

Patients who responded and remained on CCI-779 for long periods experienced an abnormal taste, which resulted in a decreased appetite and weight loss. One patient with a partial response had grade 3 weight loss due to the dysgeusia and could not restart CCI-779. Although mucositis was common, all but two cases were grade 1 or 2.

It is known that CCI-779 can cause thrombocytopenia and indeed in this study it was the most common side effect. There were several reasons why thrombocytopenia was so commonly encountered in this study. Firstly, patients could enter the protocol with grade 1 thrombocytopenia ($\geq$75,000) and could receive 100% of the CCI-779 dose if the platelet count was $\geq$50,000 (grade 2). Secondly, the patients that enrolled in this study were heavily pretreated, and thirdly most patients had marrow infiltrated with MCL cells resulting in poor marrow reserve.

Single agent CCI-779 had substantial anti-tumor activity in relapsed MCL. This study demonstrated that CCI-779 produces therapeutic benefit.

Example 2

Anti-Tumor Activity of Low Dose of Single-Agent CCI-779 for Relapsed Mantle Cell Lymphoma Eleven patients (4 refractory, 77 relapsed, ranging from 55 to 85 years old) with MCL were enrolled in a Phase II study of CCI-779 and were treated as described in Example 1 above, with the exception that they received a 10-fold lower dose than in Example 1, i.e., 25 mg/week. Eight patients (73%) were in stage 4, two (18%) in stage 3, and 4 (36%) had ≧2 extranodal sites. Patients had received a median of 3 prior therapies (range, 1-7) and 3 were refractory to their last treatment.

The overall response rate was 64% (7/11) with 7 PRs (64%).

Example 3

A dose of CCI-779 as mentioned in Example 1 or Example 2 is packaged in a container to provide a course of treatment for a patient.

All documents identified herein are incorporated by reference. One of skill in the art will recognize that minor modifications to the conditions and techniques described in the specific embodiments described herein can be varied without departing from the present invention. Such minor modification and variants are within the scope of the invention as defined by the following claims.

The invention claimed is:

1. A regimen for treating mantle cell lymphoma in a human patient, said regimen comprising delivering to the patient rapamycin 42-ester with 3-hydroxy-2-(hydroxymethyl)-2-methylpropionic acid (CCI-779) as a single active agent in a monthly cycle of treatment, said monthly cycle comprising administering a first intravenous dosage of CCI-779 comprising about 175 mg to about 250 mg per week for at least one week in the cycle followed by a decreased intravenous dose of CCI-779 of about 25 mg to 75 mg for at least one week of the cycle.

2. The regimen according to claim 1, wherein the CCI-779 is delivered via a parenteral formulation comprising from 2.5 mg/mL to 10 mg/mL CCI-779, an antioxidant comprising d,l-tocopherol, ethanol, polyethylene glycol, a surfactant, and citric acid at a concentration of less than 0.01% w/v.

3. The regimen according to claim 1, wherein the monthly cycle comprises at least one week where no CCI-779 is administered.

4. The regimen according to claim 1, wherein the monthly cycle comprises weekly dosage administrations.

5. The regimen according to claim 1, wherein the CCI-779 is delivered for two to twelve cycles.

6. The regimen according to claim 1, wherein the monthly cycles are continuous.

7. The regimen according to claim 1, wherein the first dosage of CCI-779 is about 175 mg.

8. A regimen for reducing tumor size in a relapsed mantle cell lymphoma human patient, said regimen comprising intravenously delivering to the patient a monthly cycle which comprises an intravenous dosage of about 175 to about 250 mg of CCI-779 per week as a single active agent followed by at least one weekly administration of a decreased intravenous dosage of about 75 mg per week.

9. The regimen according to claim 8, wherein the CCI-779 is delivered via a parenteral formulation comprising from 2.5 mg/mL to 10 mg/mL CCI-779, an antioxidant comprising d,l-tocopherol, ethanol, polyethylene glycol, a surfactant, and citric acid at a concentration of less than 0.01% w/v.

10. The regimen according to claim 8, wherein the dosage of CCI-779 differs from week to week within the cycle.

11. The regimen according to claim 8, wherein the monthly cycle comprises weekly or bi-weekly dosage administrations.

12. The regimen according to claim 11, wherein the CCI-779 is delivered for two to twelve cycles.

13. The regimen according to claim 8, wherein the first dosage of CCI-779 is about 175 mg.

* * * * *